United States Patent [19]

Helsley et al.

[11] Patent Number: 4,853,384

[45] Date of Patent: Aug. 1, 1989

[54] 1-CARBONYL DERIVATIVES OF 4-ARYL-4-ARYLOXYPIPERIDINES

[75] Inventors: Grover C. Helsley, Pluckemin; Larry Davis, Sergeantsville; Gordon E. Olsen, Somerset, all of N.J.

[73] Assignee: Hoechst-Roussel Pharmaceuticals Inc., Somerville, N.J.

[21] Appl. No.: 167,929

[22] Filed: Mar. 14, 1988

[51] Int. Cl.$^4$ .................. A61K 31/445; C07D 211/44
[52] U.S. Cl. ..................................... 514/255; 514/318; 514/321; 514/322; 514/323; 514/326; 514/314; 544/336; 546/194; 546/198; 546/199; 546/209; 546/210; 546/213; 546/175
[58] Field of Search ............... 546/210, 217, 194, 168, 546/199, 213, 209, 210, 198, 175; 514/326, 327, 255, 318, 321, 322, 323, 314; 544/406, 336

[56] References Cited

U.S. PATENT DOCUMENTS 2,850,500  9/1958  Elpern .................................. 546/217
3,996,366  12/1976  Baker et al. ......................... 546/210
4,325,953  4/1982  Shepherd ............................ 546/217

FOREIGN PATENT DOCUMENTS 2060619  5/1981  United Kingdom ............... 546/210

OTHER PUBLICATIONS

Boswell et al., *J. Med. Chem.*, vol. 17, No. 9, pp. 1000–1008 (1974).
Helsley et al., *J. Med. Chem.*, vol. 21, No. 3, pp. 309–312 (1978).
Derwent Abstract 33107D/19, 9/14/79.
Derwent Abstract 12127D/08, 8/3/79.

*Primary Examiner*—Mary C. Lee
*Assistant Examiner*—Zinna Northington
*Attorney, Agent, or Firm*—Raymond R. Wittekind

[57] ABSTRACT

1-Carbonyl derivatives of 4-aryl-4-aryloxypiperidines and methods for alleviating pain and treating convulsions utilizing compounds or compositions thereof are disclosed.

38 Claims, No Drawings

1-CARBONYL DERIVATIVES OF 4-ARYL-4-ARYLOXYPIPERIDINES

This invention relates to 1-carbonyl derivatives of 4-aryl-4-aryloxypiperidines. More particularly, this invention relates to 4-aryl-4-aryloxypiperidines of the formula:

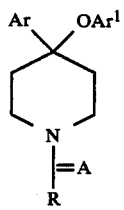

FORMULA I wherein Ar is phenyl optionally substituted by one or more loweralkyl, loweralkoxy, halogen, or trifluoromethyl groups; $Ar^1$ is phenyl optionally substituted by one or more halogen, nitro, amino or trifluoromethyl groups; A is oxygen or sulfur; and R is hydrogen, loweralkyl, arylloweralkyl, heteroarylloweralkyl, amino, loweralkylamino, diloweralkylamino, or arylamino, which compounds, alone or in combination with one or more pharmaceutically acceptable carriers, are useful for alleviating pain, and treating convulsions.

Throughout the specification and appended claims a given formula or name shall encompass the stereo, optical, and geometrical isomers thereof, as well as the pharmaceutically acceptable acid addition salts and solvates (e.g., hydrates) of same.

Subgeneric to the 4-aryl-4-aryloxypiperidines of this invention are Formula I compounds wherein
(a) Ar is

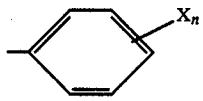

wherein X is loweralkyl, loweralkoxy, halogen, or trifluoromethyl and n is an integer having a value of 0 or 1;
(b) $Ar^1$ is

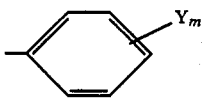

wherein Y is halogen, nitro, amino, or trifluoromethyl and m is an integer having a value of 0 or 1;
(c) $Ar^1$ is

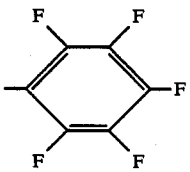

(d) A is oxygen;
(e) A is sulfur;
(f) R is hydrogen;
(g) R is loweralkyl;
(h) R is amino;
(i) R is loweralkylamino;
(j) R is diloweralkylamino;
(k) R is arylamino;
(l) R is arylloweralkyl; and
(m) R is heteroarylloweralkyl.

As used throughout the specification and appended claims the term "loweralkyl" shall mean a linear or branched, acyclic hydrocarbon radical containing no unsaturation and having the formula $-C_xH_{2x+1}$ wherein x is an integer having a value of 1 to 7, inclusive, such as methyl, ethyl, 1-propyl, 2-propyl, 1-butyl, 1-pentyl, 2-pentyl, 3-hexyl, 4-heptyl, and the like; the term "loweralkoxy" shall mean an acyclic organic of the formula $-OC_xH_{2x+1}$ wherein x is an integer having a value of 1 to 7, inclusive, such as methoxy, ethoxy, 1- and 2-propoxy, 1,2-dimethylethoxy, 1-butoxy, 1- and 2-pentoxy, 3-hexoxy, 4-heptoxy and the like; the term "halogen" shall mean a member of the group consisting of fluorine, chlorine, bromine, and iodine radicals; the term "aryl" shall mean a phenyl group optionally substituted by one or more substitutents selected from the group consisting of halogen, loweralkyl, loweralkoxy, and trifluoromethyl; the term "arylloweralkyl" shall mean a loweralkyl group having an aryl substituent thereon; the term "heteroaryl" shall mean an aromatic heterocyclic mono- or dicyclic radical such as, for example, pyridyl, pyrazinyl, quinolinyl, benzimidazolyl, thienyl, thiazolyl, imidazolyl, benzisoxazolyl, and the like, optionally substituted by one or more substituents selected from the group consisting of halogen, loweralkyl, and loweralkoxy; the term "heteroarylloweralkyl" shall mean a loweralkyl group having a heteroaryl substituent thereon; the term "amino" shall mean a group of the formula $-NH_2$; the term "loweralkylamino" shall mean an amino group substituted at the nitrogen atom thereof by a loweralkyl group; and the term "arylamino" shall mean an amino group substituted at the nitrogen atom thereof by an aryl group.

The compounds of this invention are prepared by any of several processes illustrated in the attached Reaction Scheme.

For example, in a process similar to that described in UK Patent Application No. GB 2 060 619 A at page 1, lines 14–37, a carbonyl derivative of a 4-hydroxy-4-phenylpiperidine 1 is treated with an alkali metal hydride or organolithium compound (e.g. potassium hydride, sodium hydride, butyl lithium, and the like; sodium hydride being preferred) and the resulting anion reacted with an aryl halide 2 to afford a Formula I compound 3. Suitable solvents for the reaction of the carbonyl derivative 1 and alkali metal hydride or organolithium compound include polar aprotic solvents such as, for example, dimethylformamide, hexamethylphosphoramide, dimethylsulfoxide and the like (dimethylsulfoxide or dimethylformamide being preferred). The reaction is generally conducted at temperatures of from about 25° C. to about 100° C., preferably from about 70° C. to about 85° C. The subsequent reaction with the aryl halide 2 is ordinarily conducted without isolation of the anion intermediate at a temperature of from about 5° C. to about 50° C.

Alternatively, Formula I compounds of this invention are produced by the carbonylation of a 4-aryl-4-aryloxypiperidine 4. Carbonylation can be achieved by numerous synthetic procedures. For example, Formula I compounds wherein R is loweralkylamino or arylamino can be produced by reacting a 4-aryl-4-aryloxypiperidine 4 with an isocyanate or isothiocyanate of the formula R—N=C=O or R—N=C=S (wherein R is loweralkyl or aryl) at a temperature of from about 5° C. to about 100° C., preferably from about 25° C. to 70° C., in a suitable solvent. Suitable solvents for this reaction include aromatic hydrocarbons such as, for example, benzene, xylene, toluene, and the like, benzene being preferred.

The reaction of a piperidine 4 with nitrourea provides a convenient means of effecting aminocarbonyl substitution. The reaction of a piperidine 4 with nitrourea is typically conducted at a temperature of from about 5° C. to about 100° C., preferably from about 25° C. to about 80° C., in a nonreactive organic solvent (e.g. alkanols such as ethanol, methanol, 1- and 2-propanol, 2-methoxyethanol, and the like; ethanol being preferred).

To provide a 1-formylpiperidine 3, a piperidine 4 is reacted with formic acid and acetic anhydride at a temperature of from about 5° C. to about 50° C., preferably from about 25° C. to about 35° C. in a nonreactive organic solvent (e.g. ethereal solvents such as diethyl ether, tetrahydrofuran, 1,2-dimethoxyethane, bis(2-methoxyethyl) ether, and the like; diethyl ether being preferred).

Carbonylation of a piperidine 4 can also be accomplished by the reaction of a piperidine 4 with a halide of the formula RC(O)Z or RC(S)Z (wherein R is loweralkyl, loweralkylamino, diloweralkylamino, arylamino, arylloweralkyl or heteroarylloweralkyl, and Z is halogen, preferably chlorine). This reaction is generally conducted at a temperature of from about 0° C. to about 50° C., preferably from about 5° C. to about 25° C. in the presence of a suitable base (e.g. alkali metal carbonates or bicarbonates, tertiary amines and the like, such as for example sodium carbonate, sodium bicarbonate, potassium bicarbonate, triethylamine, and the like). Halogenated hydrocarbons (e.g. dichloromethane, chloroform, carbon tetrachloride, and the like) are representative of suitable solvents for this reaction. Chloroform and dichloromethane are preferred. Depending upon the solubility of the particular reactants, the reaction may be conducted in the presence of an appropriate co-solent (e.g. water).

Formula I compounds wherein R is a heteroarylloweralkyl are alternatively produced by reacting a piperidine 4 with, for example, chloroacetylchloride, and treating the resultant intermediate with the desired heteroaromatic compound (e.g., imidazole, pyrazole, indole, isoindole, and the like) to yield a 1-heteroarylloweralkylcarbonyl piperidine 3. The reaction is generally conducted at a temperature of from about 5° C. to about 100° C., preferably from about 10° C. to about 85° C. in a dipolar aprotic solvent as previously described; dimethylformamide being preferred.

Included among the compounds of this invention are:
1-benzylcarbonyl-4-phenyl-4-(3-trifluoromethylphenoxy)piperidine;
1-acetyl-4-phenoxy-4-(4-trifluoromethylphenyl)piperidine
1-acetyl-4-(4-methylphenyl)-4-phenoxypiperidine;
1-aminocarbonyl-4-(3-methoxyphenyl)-4-phenoxypiperidine;
4-(3-chorophenoxy)-4-(3-chlorophenyl)-1-(N-methylamino)carbonylpiperidine;
4-phenoxy-4-phenyl-1-[N-(4-trifluoromethylphenyl)amino]carbonylpiperidine;
4-(2,3,4,5,6-pentafluorophenoxy)-4-phenyl-1-thioformylpiperidine;
4-phenyl-1-thioacetyl-4-(3-trifluoromethylphenoxy)piperidine;
1-benzylthiocarbonyl-4-phenoxy-4-phenylpiperidine;
1-(N-methylamino)thiocarbonyl-4-(2,3,4,5,6-pentafluorophenoxy)-4-phenylpiperidine;
4-(2,3,4,5,6-pentafluorophenoxy)-4-phenyl-1-(N-phenylamino)thiocarbonylpiperidine;
1-aminothiocarbonyl-4-(2,3,4,5,6-pentafluorophenoxy)-4-phenylpiperidine;
4-(3,5-dichlorophenoxy)-4-(N,N-dimethylamino)thiocarbonyl-4-phenylpiperidine;
1-[2-(imidazol-1-yl)thioacetyl]4-(2,3,4,5,6-pentafluorophenoxy)-4-phenylpiperidine; and
1-(N-methylamino)thicarbonyl-4-(4-nitrophenoxy)-4-phenylpiperidine.

The compounds of this invention are useful as analgesic agents due to their ability to alleviate pain in mammals. The procedure employed to determine analgetic utility is a modification of the phenyl-p-benzoquinone writhing assay in mice, a standard assay for analgesia [Proc. Soc. Exptl. Bio. Med., 95, 729 (1957)]. Pursuant to the modified procedure phenyl-p-benzoquinone (Eastman, 12.5 mg) is dissolved in 5 ml of 95% ethanol and the solution is diluted to a total volume of 100 ml with distilled water. The solution is administered to the subject mice intraperitoneally at a dose of 10 ml per kg of body weight. A characteristic "writhe" an inward rotation of one or more feet with twisting and turning of the trunk, drawing in of the abdominal wall, lordosis and arching of the back, is produced.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four goups of five animals (20 animals) are given the test compound

REACTION SCHEME

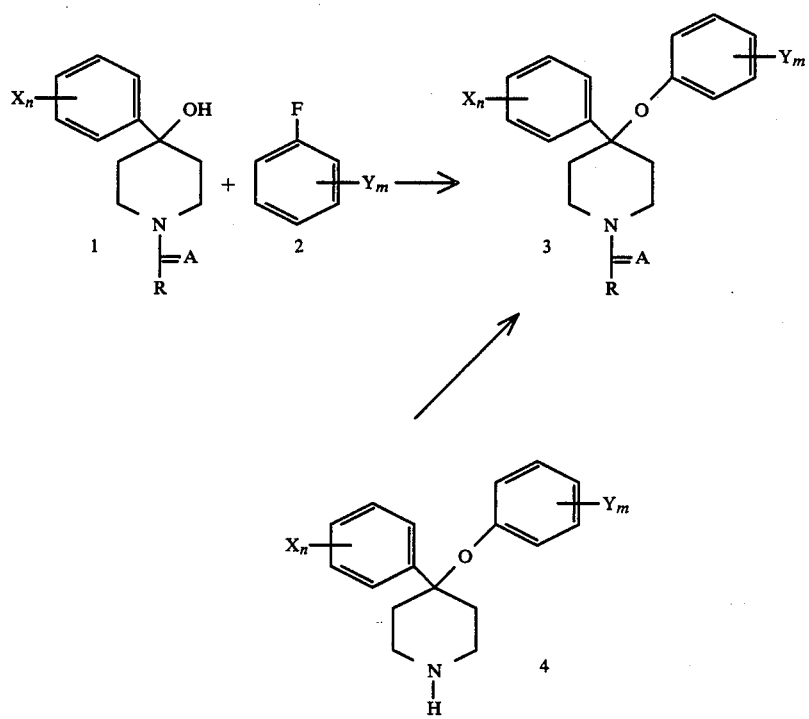

Wherein X, Y, R, A, n and m are as herein defined subcutaneously (s.c.) or orally (p.o.) at 15, 30, 45 and 60 minutes prior to administration of the phenyl-p-quinone. A control group (2 animals per group) receive an equal volume of the vehicle. After the administration of the phenyl-p-quinone, the mice are place separately in one liter beakers, and after five minutes, are observed for ten minutes. The number of writhes for each animal is recorded. The following formula is used to compute the percent inhibition:

$$\frac{\bar{x} \text{ Writhes in Control Group} - \bar{x} \text{ Writhes in Drug Group}}{\bar{x} \text{ Writhes in Control Group}} \times 100$$

The time period with the greatest percent of inhibition is considered the peak time. The results of the phenyl-p-quinone writhing assay for several of the compounds of this invention is provided in Table 1.

TABLE 1

| Compound | Analgesic Activity % Inhibition of writhing at a screening dose of 20 mg/kg, s.c. |
|---|---|
| 1-acetyl-4-phenyl-4-(4-trifluoromethylphenoxy)-piperidine | 32 |
| 1-(methylamino)carbonyl-4-(4-nitrophenoxy-4-phenyl-piperidine | 34 |
| 1-aminocarbonyl-4-(4-nitrophenoxy)-4-phenyl-piperidine | 42 |
| 1-acetyl-4-(2,3,4,5,6-pentafluorophenoxy)-4-phenylpiperidine | 38 |
| 1-acetyl-4-phenyl-4-(3-trifluoromethyl-phenoxy)piperidine | 48 |
| 1-acetyl-4-(3-chloro-phenoxy)-4-phenylpiperidine | 33 |

TABLE 1-continued

| Compound | Analgesic Activity % Inhibition of writhing at a screening dose of 20 mg/kg, s.c. |
|---|---|
| asprin | 33 |

Analgesia production is achieved when the compounds of this invention are administered to a subject requiring such treatment as an effective oral, parenteral or intravenous dose of from 0.1 to 50 mg/kg of body weight per day.

The compounds of this invention are also useful as anticonvulsants due to their anticonvulsant activity in mammals. Anticonvulsant activity is measured in male mice using the supramaximal electroshock (SES) assay described in *Arch. Int. Pharmacodyn.* 92, pp. 97–107, (1952) and the metrazol lethality assay (MTZ) described in *J. Pharmacol. Exp. Ther.*, 81, 402 (1944).

Groups of male mice (Charles River, CD-1) weighing 18 to 30 g are employed in the SES assay. Test compounds are dissolved in distilled water, or if insoluble, suspended in water containing one drop of a surfactant, such as Tween-80. Test compounds are generally administered intraperitoneally at a dose of 10 ml of solution, or suspension, per kg of animal body weight. The output terminals of an A.C. shocker, which delivers 206 volts rms for 300 msec, are placed across the animals' eyes, an electrode paste coating assuring contact of the terminals with the eyes. The test compound is administered and thereafter the subject animals are shocked.

A test compound is considered to give protection if the mouse does not exhibit extensor tonus. Protection is expressed as normalized percent inhibition relative to vehicle control.

normalized % inhibition =

$$\frac{\left[\frac{\#Rx\ Protected\ -\ \#Control\ Protected}{\#Rx\ Tested\ -\ \#Control\ Tested}\right]}{1 - \left[\frac{\#Control\ Protected}{\#Control\ Tested}\right]} \times 100$$

A time response is carried out using 6 animals per group. Animals are tested at 30, 60 and 120 minutes post drug. Additional time periods are tested if indicated by previous tests. A dose range determination is generally reserved for those compounds which inhibit convulsions by greater than about 45–55% at the screening dose employed at the time the test was performed. When the peak activity time has been determined, a dose response is initiated, using 10 animals per group at that time period.

Groups of male mice (Charles River, CD-1), weighing 18 to 30 grams are employed in the Metrazol lethality assay. Test compounds are dissolved in distilled water or if insoluble, suspended in water, to which a surfactant, such as Tween-80 is added. The test compounds are administered orally, the administered dose being dissolved or suspended in 10 ml of solution or suspension per kg of animal body weight. Control animals (2 mice/group) receive water or water and Tween-80, i.e., the vehicle for administration of the test compound. Metrazol (pentylenetetrazol) is dissolved in water (concentration 225 mg of Metrazol/10 ml of solution), and the solution is administered subcutaneously to groups of five animals each at one or more time intervals of 15, 30, 60, 90, or 120 minutes after administration of the test compound. The number of animal alive 15 minutes after treatment with Metrazol is determined and recorded. The following formula is employed to calculate the percent protection against Metrazol lethality.

% protection = $\frac{\text{number of surviving mice}}{\text{number of treated mice}} \times 100$ A dose range determination is performed by substantially the same procedure as the time response determination. In the dose range determination, five groups of 10 animals per group are employed. This determination is generally reserved for those compounds which protect against lethality by greater than 70% at the screening dose employed.

The anticonvulsant activity of several of the compounds of this invention as per the SES and MTZ assay procedures is provided in Table 2.

TABLE 2

| Compound | Anticonvulsant Activity | |
|---|---|---|
|  | MTZ ED$_{50}$, mg/kg p.o. | SES ED$_{50}$, mg/kg i.p. |
| 1-acetyl-4-phenyl-4-(4-trifluoromethylphenoxy)-piperidine | 44.8 | 32.1 |
| 1-(methylamino)carbonyl-4-(2,3,4,5,6-pentafluorophenoxy)-4-phenylpiperidine | 64.3 |  |
| 1-(methylamino)carbonyl-4-(4-nitrophenoxy)-4-phenyl-piperidine | 55.2 |  |
| 1-acetyl-4-(2,3,4,5,6-pentafluorophenoxy)-4-phenylpiperidine | 60.5 |  |
| 1-(methylamino)carbonyl-4-phenyl-4-(4-trifluoromethyl-phenoxy piperidine | 41.2 |  |
| 1-acetyl-4-(3-chloro-phenoxy)-4-phenylpiperidine |  | 55.4 |
| 1-(methylamino)carbonyl-4-phenyl-4-(3-trifluoromethyl-phenoxy)piperidine |  | 43.5 |
| 1-[2-(imidazol-1-yl)acetyl]-4-(2,3,4,5,6-pentafluoro-phenoxy)-4-phenylpiperidine | 38.0 |  |
| phenobarbital | 16.9 | 8.4 |

Anticonvulsant activity is achieved when the compounds of this invention are administered to a subject requiring such treatment at an effective oral, parenteral or intravenous dose of from 10 to 100 mg/kg of body weight per day.

It is to be understood that the dosages set forth above with respect to analgesic and anticonvulsant activity for any particular subject should be adjusted according to the individual need and the professional judgment of the person administering or supervising the administration of the aforesaid compound. It is further understood that the dosages set forth herein are exemplary only and that they do not, to any extent, limit the scope or practice of the invention.

Effective amounts of the compounds of the present invention may be administered to a subject by any one of various methods, for example, orally as in capsules or tablets, parenterally in the form of sterile solutions or suspensions, and in some cases intravenously in the form of sterile solutions. The compounds of this invention, while effective themselves, may be formulated and administered in the form of their pharmaceutically acceptable acid addition salts for purposes of stability, convenience, increased solubility and the like.

Preferred pharmaceutically acceptable acid addition salts include salts of mineral acids, for example, hydrochloric acid, sulfuric acid, nitric acid and the like, salts of monobasic carboxylic acids such as, for example, carboxysuccinic acid, citric acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; and excipient such as starch or lactose, a disintegrating agent such as alginic acid, Promogel ®, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring. When the dosage unit is a capsule, it may contain, in addition to materials of the preceeding type, a liquid carrier such as a fatty oil. Other dosage unit forms may contain other various materials which modify the physical form of the dosage unit such as, for example, coatins. Thus, tablets or pills may be coated with sugar, shellac, or other enteric coating agents. A syrup may contain, in addition to the active compounds, sucrose and/or flavorings. Materials used in preparing these various compositions shoud be pharmaceutically pure and nontoxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidnts such as ascorbic acid or sodium bisulfite; chelating agents such as ethylenediaminetetraacetic acid; buffers such as acetates, citrates or phosphates; and agents for the adjustment of tonicity such as sodium chloride or dextrose. The parenteral preparation can be enclosed in ampules, disposable syringes or multiple dose vials made of glass or plastic.

EXAMPLES

The following Examples are for illustrative purposes only and are not to be construed as limiting the invention.

EXAMPLES

Example 1

1-Acetyl-4-phenyl-4-(4-trifluoromethylphenoxy)piperidine

A stirred suspension of sodium hydride (60% in oil, 2.0 g) in 50 ml of dimethylformamide was treated with a solution of 9.8 g of 1-acetyl-4-hydroxy-4-phenylpiperidine in 80 ml of dimethylformamide and then heated at 70° C. for 1 hour. After cooling to room temperature a solution of 8.06 g of 4-fluorobenzotrifluoride in 20 ml of dimethylformamide was added dropwise and the reaction allowed to proceed for 25 hours. The reaction mixture was then poured into 400 ml of ice water and the aqueous suspension extracted with ethyl acetate. The organic layer was washed with water, dried over anhydrous magnesium sulfate, filtered, and concentrated to an oil. High pressure liquid chromatography of the oil (silica gel; elution with a 10% solution of ethyl acetate in dichloromethane) afforded 5.3 g of 1-acetyl-4-phenyl-4-(4-trifluoromethylphenoxy)piperidine, m.p. 96°–100° C.

ANALYSIS

Calculated for $C_{20}H_{20}F_3NO_2$: 66.12%C, 5.51%H, 3.86%N, Found: 66.09%C, 5.21%H, 3.81%N.

Example 2

1-Acetyl-4-phenyl-4-(3-trifluoromethylphenoxy)piperidine

A stirred suspension of sodium hydride (60% in oil, 1.8 g) in 35 ml of dimethylformamide was treated with a solution of 9.00 g of 1-acetyl-4-hydroxy-4-phenylpiperidine in 100 ml of dimethylformamide and heated at 70° C. until evolution of gas had ceased. A solution of 7.38 g of 3-fluorobenzotrifluoride in 20 ml of dimethylformamide was added, dropwise, and the reaction allowed to proceed at 70° C. for 20 hours. The reaction mixture was then poured into an ice/water mixture and the aqueous suspension extracted with ethyl acetate. The organic layer was washed with water, dried over anhydrous magnesium sulfate, filtered and concentrated to an oil. High pressure liquid chromatography of the oil (silica gel; elution with 50% ethyl acetate/dichloromethane) afforded 3.11 g (20.90%) of 1-acetyl-4-phenyl-4-(3-trifluoromethylphenoxy)piperidine, m.p. 100°–103° C.

ANALYSIS

Calculated for $C_{20}H_{20}F_3NO_2$: 66.11%C, 5.51%H, 3.87%N, Found: 66.15%C, 5.79%H, 3.73%N.

Example 3

1-Acetyl-4-(4-nitrophenoxy)-4-phenylpiperidine

A stirred suspension of sodium hydride (60% in oil, 1.00 g) in 50 ml of dimethylformamide was treated with a solution of 4.0 g of 1-acetyl-4-hydroxy-4-phenylpiperidine in 100 ml of dimethylformamide. The mixture was heated at 70° C. until evolution of gas had ceased. After cooled to ice bath temperature, a solution of 2.96 g of 1-fluoro-4-nitrobenzene in 40 ml of dimethylformamide was added, dropwise, and the reaction allowed to proceed for 20 hours. The reaction mixture was then poured into ice water and the aqueous suspension extracted with ethyl acetate. The organic layer was washed with water, dried over anhydrous magnesium sulfate, filtered, and concentrated to an oil. High pressure liquid chromatography of the oil (silica gel; elution with 20% ethyl acetate/dichloromethane) afforded 4.73 g (77.29%) of 1-acetyl-4-(4-nitrophenoxy)-4-phenylpiperidine, m.p. 145°–150° C.

ANALYSIS

Calculated for $C_{19}H_{20}N_2O_4$: 67.06%C, 5.88%H, 8.24%N, Found: 66.91%C, 5.91%H, 8.22%N.

Example 4

1-Acetyl-4-(3-chlorophenoxy)-4-phenylpiperidine

A stirred suspension of sodium hydride (60% in oil 3.28 g) in 100 ml of dimethylsulfoxide was heated at 70° C. until evolution of gas had ceased. After cooling to room temperature a solution of 10.70 g of 1-chloro-3-fluorobenzene in 40 ml of dimethylsulfoxide was added, dropwise, and the reaction mixture stirred for seven hours at 70° C. The reaction mixture was then poured into ice water and the aqueous suspension extracted with ethyl acetate. The organic layer was washed with water, dried over anhydrous mangesium sulfate, filtered and concentrated. High pressure liquid chromatography of the concentrate (silica gel; elution with ethyl acetate) afforded 2.11 g (8.6%) of 1-acetyl-4-(3-chlorophenoxy)-4-phenylpiperidine as an oil.

ANALYSIS

Calculated for $C_{19}H_{20}ClNO_2$: 69.19%C, 6.11%H, 4.25%N, Found: 68.79%C, 6.12%H, 4.19%N.

Example 5

1-(N-Methylamino)carbonyl-4-(4-nitrophenoxy)-4-phenylpiperidine

To a stirred solution of 4.9 g of 4-(4-nitrophenoxy)-4-phenylpiperidine in 50 ml of benzene was added, dropwise, a solution of 0.91 g of methyl isocyanate in 15 ml of benzene. The reaction mixture was stirred at room temperature for two hours. Evaporation of the volatiles afforded a solid which was purified by means of high pressure liquid chromatography (silica gel; elution with 50% ethyl acetate/dichloromethane) to yield 6.05 g of 1-(N-methylamino)carbonyl-4-(4-nitrophenoxy)-4-phenylpiperidine, m.p. 110°–115° C.

ANALYSIS

Calculated for $C_{19}H_{21}N_3O_4$: 64.23%C, 5.92%H, 11.83%N, Found: 64.10%C, 5.99%H, 11.85%N.

Example 6

1-Aminocarbonyl-4-(4-nitrophenoxy)-4-phenylpiperidine

To a stirred solution of 4.0 g of 4-(4-nitrophenoxy)-4-phenylpiperidine in 50 ml of 95% ethanol was added 1.68 g of nitrourea in 50 ml of 95% ethanol. The reaction mixture was refluxed for two hours and then poured into 200 ml of water. The aqueous suspension was extracted with dichloromethane. The organic layer was washed with water, dried over anhydrous magnesium sulfate, filtered and concentrated. The resulting solid was purified by high pressure liquid chromatography (silica gel; elution with 5% methanol/dichloromethane) to yield 4.04 g (91.20%) of 1-aminocarbonyl-4-(4-nitrophenoxy)-4-phenylpiperidine, m.p. 203°–206° C.

ANALYSIS

Calculated for $C_{18}H_{19}N_3O_4$: 63.34%C, 5.57%H, 12.32%N, Found: 62.87%C, 5.56%H, 12.21%N.

Example 7

1-(N-Methylamino)carbonyl-4-phenyl-4-(4-trifluoromethylphenoxy)piperidine

To a solution of 3.89 g of 4-phenyl-4-(4-trifluoromethylphenoxy)piperidine in 25 ml of benzene was added a solution of 0.68 g of methyl isocyanate in 25 ml of benzene. The reaction mixture was stirred for four hours at room temperaure. Evaporation of the volatiles afforded a solid which was purified by means of high pressure liquid chromatography (silica gel; elution with 50% ethyl acetate/dichloromethane). Recrystallization from 30% hexane/isopropyl ether yielded 2.46 g (54.19%) 1-(N-methylamino)carbonyl-4-phenyl-4-(4-trifluoromethylphenoxy)piperidine, m.p. 118°–120° C.

ANALYSIS

Calculated for $C_{20}H_{21}F_3N_2O_2$: 63.49%C, 5.55%H, 7.41%N, Found: 63.66%C, 5.68%H, 7.50%N.

Example 8

1-Aminocarbonyl-4-phenyl-4-(4-trifluoromethylphenoxy)piperidine

To stirred solution of 3.70 g of 4-phenyl-4-(4-trifluoromethylphenoxy)piperidine in 100 ml of ethanol was added 1.51 g of nitrourea. The reaction mixture was refluxed for three hours and then poured into water. The aqueous suspension was extracted with ethyl acetate. The organic layer was washed with water, dried over anhydrous magnesium sulfate, filtered and concentrated. The resulting solid was purified by means of high pressure liquid chromatography (silica gel; elution with 5% methanol/dichloromethane) to yield 3.00 g (68.65%) of 1-aminocarbonyl-4-phenyl-4-(4-trifluoromethylphenxoy)piperidine, m.p. 162°–166° C.

ANALYSIS

Calculated for $C_{19}H_{19}F_3N_2O_2$: 62.63%C, 5.26%H, 7.68%N, Found: 62.73%C, 5.25%H, 7.58%N.

EXAMPLE 9

1-(N,N-Dimethylamino)carbonyl-4-phenyl-4-(4-trifluoromethylphenoxy)piperidine

To a stirred solution of 10 g of potassium carbonate in 50 ml of water was added a solution of 4.0 g of 4-phenyl-4-(4-trifluoromethylphenoxy)piperidine in 50 ml of chloroform. After the dropwise addition of a solution of 2.5 ml of dimethylcarbonyl chloride in 30 ml of chloroform the reaction was allowed to proceed for 20 hours. The organic layer was then separated, washed with water, dried over anhydrous magnesium sulfate, filtered, and concentrated. The concentrate was purified by means of high pressure liquid chromatography (silica gel; elution with 10% ethyl acetate/dichloromethane) to yield 4.18 g (88.94%) of 1-(N,N-dimethylamino)carbonyl-4-phenyl-4(4-trifluoromethylphenoxy)piperidine, m.p. 158°–160° C.

ANALYSIS

Calculated for $C_{21}H_{23}F_3N_2O_2$: 64.29%C, 5.87%G, 7.14%N, Found: 63.89%C, 5.99%H, 7.05%N.

Example 10

1-(N-Methylamino)carbonyl-4-phenyl-4-(3-trifluoromethylphenoxy)piperidine

To a solution of 2.22 g of 4-phenyl-4-(3-trifluoromethylphenoxy)piperidine in 50 ml of benzene was added 0.40 g of methyl isocyanate. The reaction mixture was stirred at room temperature for 2.5 hours. Evaporation of the volatile afforded an oil which was purified by means of high pressure liquid chromatography (silica gel; elution with 50% ethyl acetate/dichloromethane) to yield 2.04 g (77%) of 1-(N-methylamino)carbonyl-4-phenyl-4-(3-trifluoromethylphenoxy)piperidine, m.p. 124°–127° C.

ANALYSIS

Calculated for $C_{20}H_{21}F_3N_2O_2$: 63.49%C, 5.55%H, 7.41%N, Found: 63.07%C, 5.66%H, 7.25%N.

Example 11

1-Aminocarbonyl-4-(2,3,4,5,6-pentafluorophenoxy)-4-phenylpiperidine

Step 1

A suspension of sodium hydride (60% in oil, 6.4 g) in 50 ml of dry dimethylformamide was treated with a solution of 2.5 g of 4-hydroxy-4-phenylpiperidine in 100 ml of dry dimethylformamide over a period of ten minutes. After heating at 50° C. for 30 minutes the mixture was cooled to 5° C. and a solution of 18.6 ml of hexafluorobenzene in 100 ml of dry dimethylformamide was added, dropwise, over a period of 30 minutes. The reaction mixture was then stirred at ambient temperature for 20 hours, poured into 500 ml of water, and extracted with ethyl acetate. The organic layer was washed with water, dried over anhydrous magnesium sulfate, filtered, and concentrated to yield 21 g (44%) of 4-(2,3,4,5,6-pentafluorophenoxy)-4-phenylpiperidine.

Step 2

A mixture of 4.89 g of 4-(2,3,4,5,6-pentafluorophenoxy)-4-phenylpiperidine, 50 ml of 95% ethanol and 2.1 g of nitrourea was refluxed at 70° C. until the evolution of gas had ceased. After refluxing for an additional 30 minutes, the mixture was cooled, treated with 200 ml of water and extracted with dichloromethane. The organic layer was washed with water, dried over anhydrous magnesium sulfate, filtered, and concentrated. The concentrate was purified by means of high pressure liquid chromatography (silica gel; elution with ethyl acetate) to yield 3.5 g (64.81%) of 1-aminocarbonyl-4-(2,3,4,5,6-pentafluorophenoxy)-4-phenylpiperidine, m.p. 155°–160° C.

ANALYSIS

Calculated for $C_{18}H_{15}F_5N_2O_2$: 55.96%C, 3.89%H, 7.25%N, Found: 56.00%C, 4.09%H, 7.15%N.

Example 12

1-(N-Methylamino)carbonyl-4-(2,3,4,5,6-pentafluorophenoxy)-4-phenylpiperidine

A solution of 5.0 g of 4-(2,3,4,5,6-pentafluorophenoxy)-4-phenylpiperidine in 50 ml of benzene was treated with a solution of 0.9 g of methyl isocyanate in 20 ml of benzene over a period of ten minutes. The reaction mixture was then stirred at ambient temperature for two hours. Evaporate of the volatiles afforded a solid which was purified by means of high pressure liquid chromatography (silica gel; elution with 50% ethyl acetate/dichloromethane) to yield 4.0 g (69%) of 1-(N-methylamino)carbonyl-4-(2,3,4,5,6-pentafluorophenoxy)-4-phenylpiperidine, m.p. 87°–89° C.

ANALYSIS

Calculated for $C_{19}H_{17}F_5N_2O_2$: 57.00%C, 4.28%H, 7.00%N, Found: 57.06%C, 4.45%H, 6.99%N.

Example 13

1-(N,N-Dimethylamino)carbonyl-4-(2,3,4,5,6-pentafluorophenoxy)-4-phenylpiperidine

To a solution of 10 g of potassium carbonate in 50 ml of water was added 4.0 g of 4-(2,3,4,5,6-pentafluorophenoxy)-4-phenylpiperidine in 50 ml of chloroform. The resulting mixture was treated with a solution of 2.5 ml of dimethylcarbonyl chloride in 30 ml of chloroform and stirred at room temperature for 20 hours. The organic layer mixture was then separated, washed with water, dried over anhydrous magnesium sulfate, filtered, and concentrated. The concentrate was purified by means of high pressure liquid chromatography (silica gel; 50% ethyl acetate/dichlormethane as the eluent) to yield 4.1 g (82.5%) of 1-(N,N-dimethylamino)carbonyl-4-(2,3,4,5,6-pentafluorophenoxy)-4-phenylpiperidine, m.p. 92°–96° C.

ANALYSIS

Calculated for $C_{20}H_{19}F_5N_2O_2$: 57.98%C, 4.59%H, 6.76%N, Found: 57.65%C, 4.56%H, 6.63%N.

Example 14

4-(2,3,4,5,6-Pentafluorophenoxy)-4-phenyl-1-(N-phenylamino)carbonylpiperidine

A solution of 5.0 g of 4-(2,3,4,5,6-pentafluorophenoxy)-4-phenylpiperidine in 40 ml of benzene was treated with a solution of 2.1 ml of phenyl isocyanate in 10 ml of benzene and then stirred at room temperature for five hours. Evaporation afforded an oil which was purified by means of high pressure liquid chromatography (silica gel; elution with 5% ethyl acetate/dichloromethane to yield 2.2 g (32%) of 4-(2,3,4,5,6-pentafluorophenoxy-4-phenyl-1-(N-phenylamino)carbonylpiperidine.

ANALYSIS

Calculated for $C_{24}H_{19}F_5N_2O_2$: 62.33%C, 4.14%H, 6.06%N, Found: 62.17%C, 4.34%H, 5.94%N.

Example 15

1-Acetyl-4-(2,3,4,5,6-pentafluorophenoxy)-4-phenylpiperidine

A stirred suspension of sodium hydride (60% in oil, 1.6 g) in 50 ml of dimethylformamide was treated with 7.0 g of 1-acetyl-4-hydroxy-4-phenylpiperidine in 100 ml of dimethylformamide. After the evolution of gas had ceased, the mixture was cooled to ice bath temperature and a solution of 6.88 g of hexafluorobenzene in 50 ml of dimethylformamide was added, dropwise. After stirring for 20 hours at ambient temperature the mixture was poured into ice water and then extracted with ethyl acetate. The organic layer was washed with water, dried over anhydrous magnesium sulfate, filtered and concentrated. The concentrate was purified by means of high pressure liquid chromatography (silica gel; elution with 50% ethyl acetate/dichloromethane to yield 9.06 g (73.5%) of 1-acetyl-4-(2,3,4,5,6-pentafluorophenoxy)-4-phenylpiperidine, m.p. 115°–120° C.

ANALYSIS

Calculated for $C_{19}H_{16}F_5NO_2$: 59.22%C, 4.16%H, 3.64%N, Found: 59.12%C, 4.03%H, 3.63%N.

Example 16

1-[2-(Imidazol-1-yl)acetyl]-4-(2,3,4,5,6-pentafluorophenoxy)-4-phenylpiperidine

Step 1

A chilled solution of 4.0 g of 4-(2,3,4,5,6-pentafluorophenoxy)-4-phenylpiperidine and 2.4 ml of triethylamine in 50 ml of dichloromethane was treated with a solution of 1.4 ml of chloroacetyl chloride in 10 ml of dichloromethane and then stirred at ambient temperature for four hours. The mixture was diluted with 100 ml of ethyl acetate, dried over anhydrous magnesium sulfate, filtered and evaporated to yield 5.0 g of 1-(2-chloroacetyl)-4-(2,3,4,5,6-pentafluorophenoxy)-4-phenylpiperidine as an oil.

Step 2

A mixture of 5.0 of 1-chloroacetyl-4-(2,3,4,5,6-pentafluorophenoxy)-4-phenylpiperidine, 4.0 g of imidazole, and 60 ml of dry dimethylformamide was stirred at 80° C. for five hours and then poured into 200 ml of water. The aqueous suspension was extracted with ethyl acetate. The organic layer was washed with water, dried over anhydrous magnesium sulfate, filtered and evaporated for an oil. Purification of the oil was accomplished by means of high presure liquid chromatography (silica gel; elution with 5% methanol/dichloromethane). Trituration of the resultant oil with isopropyl ether afforded a solid which was recrystallized from isopropyl ether/methanol (10:1) to afford 2.1 g of 1-[2-imidazol-1-yl)acetyl]-4-(2,3,4,5,6-pentafluorophenoxy)-4-phenylpiperidine, m.p. 120°–122° C.

ANALYSIS

Calculated for $C_{22}H_{18}F_5N_3O_2$: 58.54%C, 4.02%H, 9.31%N, Found: 58.27%C, 3.92%H, 9.09%N.

Example 17

1-Formyl-4-(2,3,4,5,6-pentafluorophenoxy)-4-phenylpiperidine

A mixture of 1.5 ml of formic acid and 3.5 ml of acetic anhydride was stirred at 55° C. for one hour, cooled and then treated with a solution of 4.0 g of 4-(2,3,4,5,6-pentafluorophenoxy)-4-phenylpiperidine in 50 ml of diethyl ether. After stirring at ambient temperature for three hours, the reaction mixture was poured into 100 ml of water, basified to a pH of about 10 by the addition of sodium bicarbonate, and extracted with ethyl acetate. The organic layer was washed with water, dried over anhydrous magnesium sulfate, filtered and concentrated to an oil. High pressure liquid chromatography of the oil (silica gel; elution with ethyl acetate) afforded a solid which was recrystallized from isopropyl ether/hexanes (1:2) to yield 2.1 g (64%) of 1-formyl-4-(2,3,4,5,6-pentafluorophenoxy)-4-phenylpiperidine, m.p. 118°–119° C.

ANALYSIS

Calculated for $C_{18}H_{14}F_5NO_2$: 58.22%C, 3.80%H, 3.77%N, Found: 58.18%C, 3.95%H, 3.76%N.

Example 18

1-(N-Methylthiocarbonyl)-4-(2,3,4,5,6-pentafluorophenoxy)-4-phenylpiperidine

A mixture of 4.0 g of 4-(2,3,4,5,6-pentafluorophenoxy)-4-phenylpiperidine and 1.5 ml of methyl thio isothiocyanate was stirred at ambient temperature for two hours and then concentrated. High pressure liquid chromatography of the concentrate (silica gel; elution with ethyl acetate/dichloromethane (1:3) afforded a solid which was recrystallized from isopropyl ether/methanol (10:1) to yield 3.0 g (62%) of 1-(N-methylthiocarbonyl)-4-(2,3,4,5,6-pentafluorophenoxy)-4-phenylpiperidine, m.p. 172°–173° C.

ANALYSIS

Calculated for $C_{19}H_{17}F_5N_2OS$: 54.80%C, 4.12%H, 6.73%N, Found: 54.74%C, 4.22%H, 6.66%N.

What is claimed is:

1. A compound of the formula:

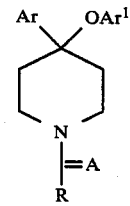

wherein Ar is phenyl optionally substituted by one or more loweralkyl, loweralkoxy, halogen, or trifluoromethyl groups; $Ar^1$ is phenyl optionally substituted by one or more halogen, nitro, amino or trifluoromethyl groups; A is oxygen or sulfur; and R is hydrogen, loweralkyl, phenylloweralkyl wherein the phenyl group is substituted by one or more substituents selected from the group consisting of halogen, loweralkyl, loweralkoxy, and trifluoromethyl, heteroarylloweralkyl wherein the heteroaryl moiety is selected from the group consisting of pyridyl, pyrazinyl, quinolinyl, benzimidazolyl, thienyl, thiazolyl, imidazolyl, and benzisoxazolyl substituted by one or more substituents selected from the group consisting of halogen, loweralkyl, and loweralkoxy, amino, loweralkylamino, diloweralkylamino, or phenylamino wherein the phenyl group is substituted by one or more substituents selected from the group consisting of halogen, loweralkyl, loweralkoxy, and trifluoromethyl.

2. A compound as defined in claim 1 wherein Ar is

wherein X is loweralkyl, loweralkoxy, halogen, or trifluoromethyl and n is an integer having a value of 0 or 1.

3. A compound as defined in claim 2 wherein A is oxygen.

4. A compound as defined in claim 3 wherein $Ar^1$ is

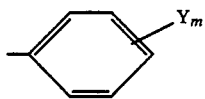

wherein Y is halogen, nitro, amino, or trifluoromethyl and m is an integer having a value of 0 or 1.

5. A compound as defined in claim 3 wherein Ar¹ is

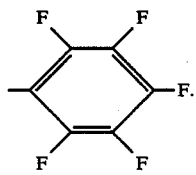

6. A compound as defined in claim 5 wherein R is hydrogen.

7. The compound of claim 6 which is 1-formyl-4-(2,3,4,5,6-pentafluorophenoxy)-4-phenylpiperidine.

8. A compound as defined in claim 4 wherein R is loweralkyl.

9. The compound of claim 8 which is 1-acetyl-4-phenyl-4-(4-trifluoromethylphenoxy)piperidine.

10. The compound of claim 8 which is 1-acetyl-4-phenyl-4-(3-trifluoromethylphenoxy)piperidine.

11. The compound of claim 8 which is 1-acetyl-4-(4-nitrophenoxy)-4-phenylpiperidine.

12. The compound of claim 8 which is 1-acetyl-4-(3-chlorophenoxy)-4-phenylpiperidine.

13. A compound as defined in claim 5 wherein R is loweralkyl.

14. The compound of claim 13 which is 1-acetyl-4-(2,3,4,5,6-pentafluorophenoxy)-4-phenylpiperidine.

15. A compound as defined in claim 4 wherein R is amino.

16. The compound of claim 15 which is 1-aminocarbonyl-4-(4-nitrophenoxy)-4-phenylpiperidine.

17. The compound of claim 15 which is 1-aminocarbonyl-4-phenyl-4-(4-trifluoromethylphenoxy)piperidine.

18. A compound as defined in claim 5 wherein R is amino.

19. The compound of claim 18 which is 1-aminocarbonyl-4-(2,3,4,5,6-pentafluorophenoxy)-4-phenylpiperidine.

20. A compound as defined in claim 4 wherein R is loweralkylamino.

21. The compound of claim 20 which is 1-(N-methylamino)carbonyl-4-(4-nitrophenoxy)-4-phenylpiperidine.

22. The compound of claim 20 which is 1-(N-methylamino)carbonyl-4-phenyl-4-(4-trifluoromethylphenoxy)piperidine.

23. The compound of claim 20 which is 1-(N-methylamino)carbonyl-4-phenyl-4-(3-trifluoromethylphenoxy)piperidine.

24. A compound as defined in claim 5 wherein R is loweralkylamino.

25. The compound of claim 24 which is 1-(N-methylamino)carbonyl-4-(2,3,4,5,6-pentafluorophenoxy)-4-phenylpiperidine.

26. A compound as defined in claim 4 wherein R is diloweralkylamino.

27. The compound of claim 26 which is 1-(N,N-dimethylamino)carbonyl-4-phenyl-4-(4-trifluoromethylphenoxy)piperidine.

28. A compound as defined in claim 5 wherein R is diloweralkylamino.

29. The compound of claim 28 which is 1-(N,N-dimethylamino)carbonyl-4-(2,3,4,5,6-pentafluorophenoxy)-4-phenylpiperidine.

30. A compound as defined in claim 5 wherein R is phenylamino wherein the phenyl group is substituted by one or more substituents selected from the group consisting of halogen, loweralkyl, loweralkoxy, and trifluoromethyl.

31. The compound of claim 30 which is 4-(2,3,4,5,6-pentafluorophenoxy)-4-phenyl-1-(N-phenylamino)carbonylpiperidine.

32. A compound as defined in claim 5 wherein R is heteroarylloweralkyl wherein the heteroaryl moiety is selected from the group consisting of pyridyl, pyrazinyl, quinolinyl, benzimidazolyl, thienyl, thiazolyl, imidazolyl and benzisoxazolyl substituted by one or more substituents selected from the group consisting of halogen, loweralkyl, and loweralkoxy.

33. The compound of claim 32 which is 1-[2-(imidazol-1-yl)acetyl]-4-(2,3,4,5,6-pentafluorophenoxy)-4-phenylpiperidine.

34. A compound as defined in claim 2 wherein A is sulfur and Ar¹ is

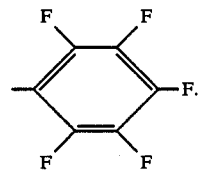

35. A compound as defined in claim 34 wherein R is amino, loweralkylamino or diloweralkylamino.

36. The compound of claim 35 which is 1-(N-methylthiocarbonyl)-4-(2,3,4,5,6-pentafluorophenoxy)-4-phenylpiperidine.

37. A pain alleviating composition comprising an inert pain-alleviating adjunct and, as the active ingredient, an amount effective in alleviating pain of a compound as defined in claim 1.

38. A method of alleviating pain comprising administering to a mammal in need of pain alleviation a pain alleviating effective amount of a compound as defined in claim 1.

* * * * *